United States Patent [19]

Malley

[11] 4,140,679
[45] Feb. 20, 1979

[54] ANTIGEN-PROTEIN COMPLEX FOR BLOCKING ALLERGIC REACTIONS

[75] Inventor: Arthur Malley, Beaverton, Oreg.

[73] Assignee: Research Corporation, New York, N.Y.

[21] Appl. No.: 731,414

[22] Filed: Oct. 12, 1976

[51] Int. Cl.$^2$ .................... C08G 69/36; A61K 39/36
[52] U.S. Cl. ......................... 260/857 R; 260/112 R; 260/121; 424/88; 424/91; 424/177
[58] Field of Search .................. 260/112 R, 121, 78 A; 424/88

[56] References Cited
PUBLICATIONS

Malley et al., *Immunochemistry*, (1975), vol. 12 (6–7), pp. 551–554.
Girard et al., *Chemical Abstracts*, vol. 83:162,003u (1975).
Malley et al., *J. of Immunology*, vol. 99, No. 4 (1967), pp. 825–830.
Malley et al., *Chemical Abstracts*, vol. 83:161,957w (1975) effective date 1974.
Sanderson et al., *Immunology*, vol. 20 (1971), pp. 1061–1065.
Axen et al., *Nature*, vol. 214, (1967), pp. 1302–1304.
Malley et al., *J. of Allergy*, vol. 43, No. 2 (1969), pp. 59–64.

*Primary Examiner*—Walter C. Danison
*Attorney, Agent, or Firm*—Dennis P. Clarke

[57] ABSTRACT

A multivalent complex suitable for blocking allergic reactions comprising (1) at least one Timothy antigen D fragment having the antigenic determinant structure:

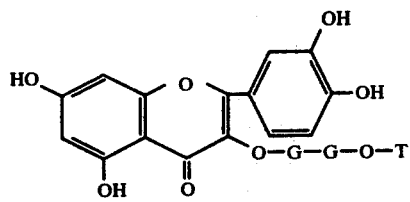

wherein:
G represents glucose, and
T represents threonine or a peptide linked to said structure through a threonine molecule;
covalently bonded through at least one glucose moiety to a peptide or protein, (2) a conjugate having the structure:

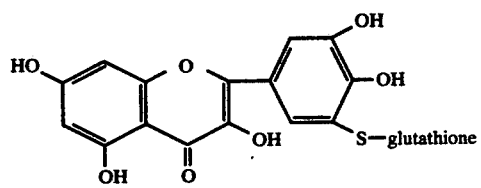

or (3) a conjugate comprising at least one conjugate of the structure:

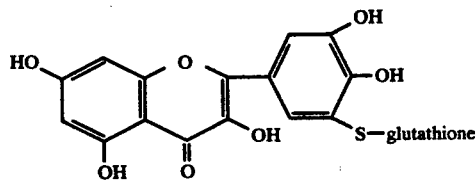

covalently bonded to a protein or peptide by a peptide linkage through the glutathione moiety.

A method of forming complex (1) by activating a glucose moiety of the Timothy antigen D fragment and reacting the thus activated intermediate with a peptide or protein.

A method of treating allergies comprising injecting one of the above complexes into an individual to inhibit antigen-induced histamine release.

An injectable composition for blocking allergic reactions containing the above complex.

24 Claims, No Drawings

ANTIGEN-PROTEIN COMPLEX FOR BLOCKING ALLERGIC REACTIONS

BACKGROUND OF THE INVENTION

Methods of treating allergies and allergic reactions have heretofore embodied the administration to an individual of an antigen which initiates the formation of antibodies which compete with the antibodies initiated by the allergen thereby dampening or reducing the allergic reaction.

The usual prior art approach in the treatment of allergic patients involves the preparation of a crude extract of the allergy-producing substance in an aqueous buffered solution. The patients are then treated with first minute, then increasing doses of the crude extract over a long period of time. Frequently, three or more years of treatment are necessary before significant lasting improvement is observed. As the treatment progresses, the amount of crude extract that a patient receives is gradually increased. The extent of increased dosage and rate depends upon the patient's individual sensitivity and the degree of reaction to previous dosages.

The injection of whole crude allergen extract over long periods of time induce the production of blocking or competing antibodies. It is theorized that the blocking antibodies compete with allergic antibody for the antigen and provide protection to the allergic patient.

There are numerous and obvious disadvantages associated with this expensive and time-consuming process of desensitizing the allergic patient. Very often the administration of the crude extract results in a severe allergic reaction if the dosages have not been carefully monitored and administered. In addition, the process of desensitization is a long and time-consuming and very often expensive process. In addition, the production of competing antibodies in the allergic patient very often result in side effects which may be more damaging to the patient than the allergic reaction itself.

More importantly, the method of desensitization heretofore employed in the prior art has not been altogether successful. In many instances, the time-consuming desensitization procedure does not result in an adequate degree of protection to the allergic patient who still continues to suffer with the allergy when exposed to antigen.

It is an object of the present invention to provide a complex suitable for administration to an allergic patient which neutralizes existing antibodies and completely blocks the formation of antibodies, either competing or specific to the allergenic antigen.

It is a further object of the invention to provide a method for the production of complexes that will block the allergic reaction.

It is still a further object of the invention to provide a method for the treatment of an allergic individual to block the allergic reaction.

It is still a further object of the present invention to provide an injectable composition for administration to an allergic patient for blocking the allergic reaction.

SUMMARY OF THE INVENTION

The invention comprises a multivalent complex suitable for blocking allergic reactions comprising (1) at least one Timothy antigen D fragment having the antigenic determinant structure:

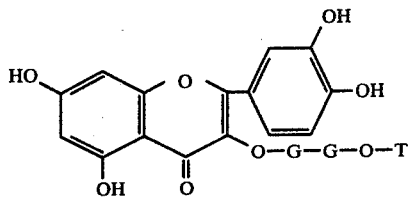

wherein:
G represents glucose, and
T represents threonine or a peptide linked to said structure through a threonine molecule;
covalently bonded through at least one glucose moiety to a peptide or protein, (2) a conjugate having the structure:

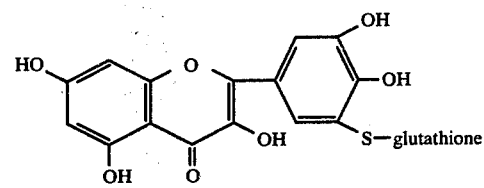

or (3) a conjugate comprising at least one conjugate of the structure:

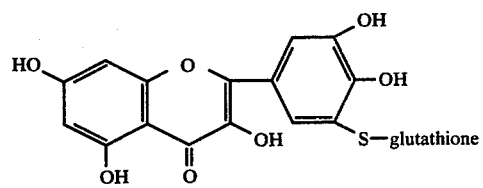

covalently bonded to a protein or peptide by a peptide linkage through the glutathione moiety.

The invention also includes a method for preparing complex (1) by activating a glucose moiety of the Timothy antigen D fragment and thereafter reacting the thus formed intermediate with a peptide or protein.

The invention further includes a method of treating allergies comprising injecting into an individual an amount of one of the above complexes sufficient to inhibit antigen-induced histamine release.

The invention further includes an injectable composition suitable for administration to allergic patients for blocking allergic reactions comprising a medium suitable for injection containing the above-identified complex.

DETAILED DESCRIPTION OF THE INVENTION

Various allergenic antigen fragments of Timothy pollen have been recently isolated and characterized. See Malley et al, *Immunochemistry*, 1975, Volume 12, pages 551–554. A major multi-valent allergen contained in Timothy pollen is that known in the prior art as antigen B. The monovalent antigenic determinant structure of antigen B which is commonly termed antigen D is:

[Structure: quercetin-like flavonoid with O—G—G—O—T substituent]

wherein:
G represents glucose, and
T represents threonine or a peptide linked to said structure through a threonine molecule.

Fragments of antigen D, identified in the prior art as antigen $D_1$, antigen $D_2$ and antigen $D_3$ differ in the size of the peptide "tail" linked to the glucose moiety of the antigenic determinant structure through the threonine molecule. [See J. Immunology 99, 825, 1967; Immunochemistry, 1, 237, 1964; 12, 551, 1975; WHO Symposium on Allergen Standardization ed. by F. T. Perkins, Geneva, 1974; Develop. Biol. Standard 29, 29, 1975]. Antigen $D_1$ has a molecular weight of about 5,000. Antigen $D_2$ has a molecular weight of about 2,500. Antigen $D_3$ is the fragment wherein the molecule bonded to the glucose moiety is threonine, alone. In some cases serine, instead of threonine, is attached to the glucose moiety due to a misreading of the code responsible for the addition of specific amino acids during protein synthesis.

The quercitin fraction of the antigen structural formula is linked to the glucose moieties via an ether linkage through OH groups on the respective molecules. The threonine linkage to the glucose moiety is also an ether linkage through an OH group on the cellobiose fraction and the OH group of threonine. It is presumed, based on stoichiometric considerations, that the activation occurs primarily at the glucose molecule adjacent to the quercitin molecule. However, it is to be understood that the complexes of the invention are formed through a glucose activation mechanism notwithstanding the precise locus of activation within the cellobiose fraction. It is not precisely known which OH group in cellobiose fraction comprises the linkage site.

As is apparent from the above structure, the molecule is open at various sites to conjugation with a wide variety of reactants. Many multivalent conjugates can be prepared which would be expected to initiate allergic reactions by virtue of their structure. Indeed, it has been found that the attachment of proteins or peptides to the molecule at sites other than the glucose or carbohydrate moieties results in conjugates which initiate allergic reactions.

Unexpectedly, it has been found that the linkage of a peptide or a protein to the antigen D fragment through the glucose moiety results in a complex which does not initiate allergic reactions, but rather, completely neutralizes allergic antibody and inhibits or blocks the formation of allergic antibodies.

Thus, these complexes or conjugates may be administered to an allergic patient for the complete inhibition of the allergic reaction without the need for the long and time-consuming and expensive desensitization process described above. Since administration of the complex inhibits the formation of allergic antibodies altogether, the allergic reaction itself is inhibited as well as any side effects produced by the formation of competing antibodies produced according to the conventional desensitization method.

Similar results have been shown to be produced by a conjugate having the structure:

[Structure: quercetin-glutathione conjugate with S—glutathione substituent]

or a conjugate comprising at least one quercitinglutathione conjugate covalently bonded to a protein or peptide by a peptide linkage through the glutathione moiety. Administration of these complexes or conjugates also results in a complete inhibition of the formation of allergic antibodies, either specific to the antigen or competing antibodies, and a complete blockage of the allergic reaction.

The Timothy antigen D fragment may be covalently bonded through at least one glucose moiety to any suitable peptide or protein. It is to be understood that any peptide or protein suitable for administration to an allergic patient may be covalently bonded to the antigen fragment. Preferred among the peptides or proteins are human serum albumin, a d-amino acid copolymer of lysine and glutamic acid (d-GL), human IgG as well as other homologous and similar proteins or d-amino acid copolymers.

As noted above, it is essential that the peptide or protein be linked to a glucose moiety of the antigen D fragment. Bonding of the protein or peptide to any other portion of the molecule will result in a complex which initiates rather than inhibits the allergic reaction. Covalent bonding may be achieved by activating the antigen D fragment with a cyanogen halide. The method is described in detail by Axen et al, *Nature*, 214, 1302-1304 (1967) and Cuatrecasas et al, *Proc. Natl. Acad. Sci.*, U.S., 61, 636-643 (1968). The cyanogen halide reacts with the hydroxyl group of the glucose moieties to form cyanate esters. The reaction occurs most rapidly at a pH between 10 and 12. The cyanate may react further with additional hydroxyl groups to form an imidocarbonate intermediate. The cyclic imidocarbonate formed as a major product following the reaction of the cyanogen halide with the glucose moiety is highly reactive with amines to form N-imidocarbonates, isoureas or N-carbamates. The exact nature of the linkage between the protein and the cyanogen halide activated glucose moiety is unknown. Notwithstanding the exact mechanism, however, the intermediate formed by the reaction of a cyanogen halide with the antigen D fragment is highly reactive with peptides and proteins to form a complex wherein the peptide or protein is covalently linked through the glucose moiety to the antigen D fragment.

The cellobiose fraction of the antigen D fragment may also be activated for linkage to the protein or peptide by the method described in Immunol. 20, 1061, (1971):

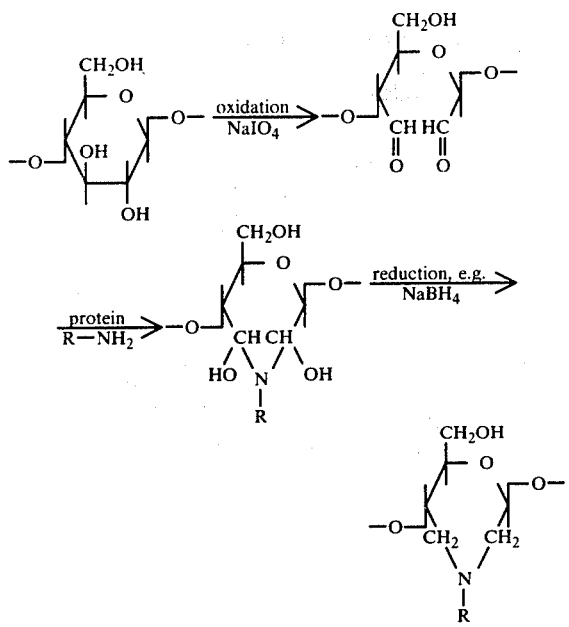

Where the carboxyl groups of the antigen D fragment were activated by Woodward's reagent K leaving the quercitin-glucose-glucose moiety unaffected, the resulting conjugate with human serum albumin, for example, induced antigen-induced histamine release reactions as shown by direct skin tests. Thus, it is apparent that the allergic reaction inhibition capabilities of the complex depend upon conjugation of the peptide or protein with the antigen-D fragment through the glucose moiety.

The quercitin-glutathione and quercitinglutathione-protein conjugates described above are also potent allergic reaction blocking agents.

The quercitin-glutathione conjugate is formed by an oxidation-addition reaction utilizing AgO or other suitable oxidizing agent:

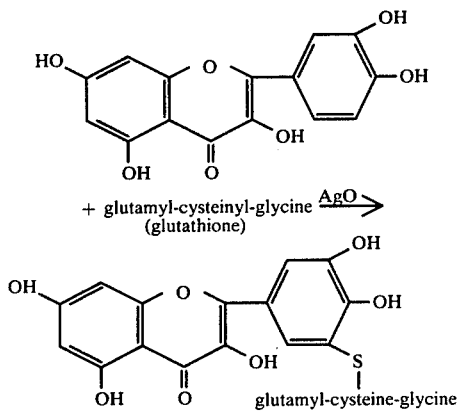

The resulting conjugate may then be conjugated with a peptide or protein by activation of the carboxyl groups of the glutathione moiety with, for example, Woodward's reagent, carbodiimides, etc., followed by conjugation with the protein or peptide molecule. The quercitinglutathione is linked to the protein via a peptide bond through either the glutamic acid or glycine portion of the glutathione moiety.

The peptide or protein conjugated to the quercitin-glutathione conjugate may be any peptide or protein suitable for administration to an allergic patient. Preferred among the proteins and peptides are human serum albumin, a d-amino acid copolymer of lysine and glutamic acid (d-GL), human IgG or other homologous proteins or d-amino acid copolymers.

Obviously, the antigen D fragment and quercitin-glutathione molecule may be bonded to the protein or peptide molecule at a variety of sites on the latter. Generally, it is preferred to bind from about 2.0 to about 30 moles, preferably 5 to 20 moles, of the antigen D fragment or quercitin-glutathione compound to 1 mole of protein or peptide. The molar ratio may be varied by varying the molar ratio of reactants in the method of preparation.

The antigen-protein complexes described above may be incorporated in any suitable medium such as buffered saline for administration to an allergic patient.

Conventional additives, adjuvants, etc., may be included in the composition for injection; however, it is to be understood that they are not required.

Generally, the compositions are injected subcutaneously, intra-muscularly or intra-venously.

Generally, dosages in the range of from about 0.01 to about 0.25 mg, preferably 0.025 to 0.1 mg, per kg body weight of the complex in the composition injected is sufficient to provide an acceptable degree of allergic reaction blocking capability.

It is to be understood that the parameters of the dosage range are governed by the duration of the complex in the circulation, the antibody titer of the patient undergoing therapy, the immune status of the patient and the duration of the suppression of the IgE response.

The complexes and methods of the present invention are useful in the treatment of grass-sensitive patients to reduce allergy symptoms. The complexes suppress the formation of allergic antibodies against grass pollen antigens and further act to neutralize existing antibodies in the patient's system. It is to be understood that the invention is useful in blocking not only Timothy allergic reactions but also rye grass and other grass pollens that cross-react with Timothy grass pollen (i.e., June grass, etc.).

The following examples illustrate methods of preparation of the complexes of the invention.

EXAMPLE 1

Preparation of Antigen D-protein Complex 90 mg of antigen $D_1$ fragment (mol wt. ~5000) were placed in an ice bath and the pH adjusted to 10.5 with NaOH solution. The mixture was provided with a motorized stirrer and 2 g CNBr was added. The pH was maintained at 10.5 ± 0.25 by the addition of NaOH over the next 10 minutes. 15 ml of 0.1 M $NaHCO_3$ buffer (pH 9) containing 0.15 M NaCl was added. Then, 45 mg of human serum albumin (HSA) was added and the mixture stirred at 4° C. for 24 hours. The mixture was concentrated under negative pressure to yield a product having an antigen $D_1$ / protein ratio of about 5:1. Unreacted antigen $D_1$ was removed by dialysis.

Complexes with antigen $D_2$ and $D_3$ fragments and other protein or peptide carriers may be prepared in identical fashion.

EXAMPLE 2

Preparation of Quercitin-Glutathione 1.5 g of AgCl was mixed with 10 ml of 4N NaOH for 20 minutes. The AgO precipitate was filtered on a Buchner funnel.

0.2 g of glutathione was dissolved in 4 ml of 0.25 N NaOH and placed in an ice bath. 0.2 g quercitin was dissolved in 8 ml of 0.25 N NaOH. 1.2 g of the freshly prepared AgO was added to the latter and the mixture stirred 15–20 minutes on an ice bath.

The glutathione solution was added and the mixture stirred for 1 hour in an ice bath. Excess AgO was removed by filtering. The pH of the resulting solution was adjusted to 1–2.5 with HCl and the solution stirred for 30 minutes.

The solution was filtered to remove unbound quercitin and the pH readjusted to 7 with NaOH. Free glutathione was determined by the DNTB method (Anal. Biochem. 48, 1557, 1972).

EXAMPLE 3

Preparation of Quercitin-Glutathione Protein Conjugate 40 mg of quercitin-glutathione was added to 100 mg of Woodward's Reagent and mixed for 10 minutes at room temperature. The pH was adjusted to 6.2 with 0.3 M cacodylate buffer (pH 6.8).

100 mg of HSA was added while maintaining the pH above 6.2. The mixture was allowed to remain at room temperature for 10–15 minutes and then overnight at 4° C. The solution was concentrated under negative pressure. Dialysis removes unbound quercitin-glutathione from its conjugate with the protein.

The conjugate with other proteins and peptides may be prepared in identical fashion.

The following example illustrates the allergic reaction inhibiting capabilities of the complexes and methods of the present invention.

EXAMPLE 4

Histamine release from monkey lung tissue passively sensitized with the serum of allergic patients is determined in accordance with the method described by Malley et al, *J. Immunol.* 100, 915 (1968). The sera employed to sensitize the monkey lung tissue was from a pool of sera from 20 Timothy-sensitive patients with an average allergic antibody titer of 1:750. The monkey lung tissue is then incubated for two hours at 37° C. with the serum. Prior to challenge with the allergen, the sensitized tissue is incubated for ten minutes at 37° C. with the inhibiting agent. The antigenic challenge is carried out by incubation with the optimum concentration of crude pollen extract (WST) for 15 minutes at 37° C.

The results are set forth in Table 1 wherein:

WST represents an aqueous extract of whole Timothy grass pollen dialyzed to remove low molecular weight fragments;

$D_1$ represents the Timothy antigen D fragments having a molecular weight of about 5000;

$D_2$ represents the Timothy antigen D fragment having a molecular weight of about 2500;

$D_3$ represents the Timothy antigen D fragment having a molecular weight of less than 1000 and comprising the complex noted above wherein T represents threonine;

HSA represents human serum albumin;

dGL represents a d-amino acid copolymer of glutamic acid and lysine having a molecular weight of about 40,000;

RhIg represents rhesus IgG.

TABLE 1

| Preparation | Method of Conjugation | Conj. Ratio | Conc. of Conjugate | WST Antigen Conc. (µg) | Direct Challenge Antigen (µg) | % Inhibition |
|---|---|---|---|---|---|---|
| WST | — | — | — | 40 | 2.7 | — |
| $D_1$ - HSA | | 6.2:1 | .260 mg | 40 | 1.27 | 53 |
| $D_1$ - RhIgG | CNBr | 15:1 | .580 mg | 40 | .14 | 95 |
| $D_1$ - dGL | | 4:1 | .500 mg | 40 | .35 | 87 |
| Quercitin-Glutathione | Oxidation and Addition | 1:1 | 1.5 mg | 40 | .32 | 88 |
| | | | .75 mg | 40 | .86 | 68 |
| | | | .37 mg | 40 | 1.2 | 55 |
| Quercitin-Glutathione-HSA | Oxidation and addition, then Woodward's Reagent K | 20:1 | 1.6 mg | 40 | .37 | 90 |
| | | | .80 mg | 40 | .70 | .74 |
| | | | .40 mg | 40 | 1.13 | 58 |

As is apparent from the results in Table 1, the complexes of the present invention are potent allergic reaction inhibitors.

The following example further illustrates the allergic reaction inhibiting capabilities of the complexes of the invention.

EXAMPLE 5

The passive transfer skin reactivity of the complexes of the invention is compared with the antigens present in Timothy pollen as well as complexes prepared by conjugating the peptide or protein to the antigen fragments through moieties other than the glucose moiety.

0.1 ml of sera containing allergic antibodies (from a pool of sera of 20 Timothy-sensitive patients-mean P-K titer of 750) was intradermally injected into the skin of a non-allergic volunteer. 48 hours later each site previously sensitized with sera were challenged with a variety of antigens and complexes. The allergic antibodies in the implanted sera interact with allergenic antigen materials to cause a localized allergic reaction. If the antigenic material does not initiate allergic reactions, no localized reaction will be observed.

The results of various tests involving the complexes of the present invention, as well as the antigen material in Timothy pollen, are set forth in Table 2.

TABLE 2

| Preparation | Method of Conjugation | Conj. Ratio | Antigen Conc. | P-K Reaction |
|---|---|---|---|---|
| WST | — | — | 1 µg | 4+ |
| $D_1$ - HSA | | 6.2:1 | 500 µg | Neg |
| $D_1$ - dGL | CNBr | 4:1 | 500 µg | Neg |
| $D_1$ - RhIgG | Activates | 20:1 | 580 µg | Neg |
| $D_2$ - RhIgG | sugar | 7.2:1 | 500 µg | Neg |
| $D_2$ - dGL | moiety | 2.8:1 | 500 µg | Neg |
| $D_3$ - HSA | | 5:1 | 500 µg | Neg |

TABLE 2-continued

| Preparation | Method of Conjugation | Conj. Ratio | Antigen Conc. | P-K Reaction |
|---|---|---|---|---|
| $D_1$ - HSA | Woodward's Reagent K | 2.6:1 | 25 μg | 2+ |
| $D_1$ - HSA | Activates COOH Groups | 4:1 | 25 μg | 4+ |
| $D_3$ - HSA | | 11.3:1 | 100 μg | 4+ |
| Quercitin-Glutathione | Oxidation and Addition | 1:1 | 1.5 mg | Neg |
| Quercitin-Glutathione-dGL | Woodward's Reagent K | 12:1 | 100 μg | Neg |
| Quercitin-Glutathione-HSA | Woodward's Reagent K | 20:1 | 1.6 mg | Neg |

The above results indicate that the complexes of the present invention do not initiate allergic reactions. It should further be noted that those complexes of the antigen D fragments conjugated with the protein through moieties other than the glucose moiety are potent initiators of allergic reactions thereby indicating the criticality of conjugation through the glucose moiety of the antigen D fragment.

EXAMPLE 6

This example illustrates the ability of the complexes of the invention to suppress the formation of allergic antibodies.

Preliminary studies demonstrated that $LAF_1$ mice developed good IgE (allergic antibodies) responses against Timothy pollen.

Animals are injected i.p. with 10 μg WST in alum and three weeks later they receive a second i.p. injection of 10 μg WST in alum. IgE titers, after the initial immunization, rise to titers between 1/100 to 1/200 as measured by PCA. IgE titers, after the second injection of antigen, rise to values between 1/600 and 1/800 as measured by PCA.

Passive cutaneous anaphylaxis (PCA) is measured by injection of 0.025 ml of serum dilution into the side of a mouse or rat. Seventy-two hours (mouse) or three hours (rat) later the animals are challenged with WST in Evans blue dye injected intravenously. Interaction of the circulating antigen and tissue-fixed IgE results in a localized allergic reaction, and the site is made visual by the leakage of the blue dye into the reacted area. The IgE titer is defined as the lowest dilution giving a positive PCA reaction.

Mouse IgE in these animals is made against the same antigenic determinant as that expressed on the antigen D fragments.

The two complexes of the invention chosen for test purposes were:
(1) Antigen $D_2$-dGL ($D_2$-dGL): a non-immunogenic copolymer of d-glutamic acid and d-lysine (MW 40,000) with an average of 2.8 antigen $D_2$ groups/mole of dGL attached. Conjugation was by modification of sugar moiety with CNBr prior to addition to dGL.
(2) Quercitin-glutathione-dGL (Q-G-dGL): prepared by conjugation of Quercitin-glutathione to dGL with an average of 12-20 Q-G groups/moles of dGL.

Administration of Q-G-dGL or $D_2$-dGL via i.p. route and given 3 days prior to secondary immunization of WST.

| day: | 0 | 18 | 21 | 28 |
|---|---|---|---|---|
| injection: | ↑ WST | ↑ $D_2$dGL or Q-G-dGL | ↑ WST | ↑ Bleed |
| | in alum | | in alum | |

Results: Control animals given saline on day 18 have the following IgE titer-600 (average response in 18 animals.)

| | IgE Titer | Animals group |
|---|---|---|
| low dose (0.12 mg $AgD_2$) | 350 | 6 |
| med. dose (0.6 mg $AgD_2$) | 300 | 6 |
| high dose (1.2 mg $AgD_2$) | < 100 | 6 |
| Animals treated with Q-G-dGL: | | |
| | IgE Titer | Animals |
| low dose (0.24 mg Quercitin) | 600 | 6 |
| med. dose (1.8 mg Quercitin) | 300 | 6 |
| high dose (3.6 mg Quercitin) | 100 | 6 |

The above data indicates that both conjugates significantly reduce IgE level when administered 3 days prior to secondary antigen injection, thereby indicating antibody neutralization and suppression. Similar tests have indicated that administrations up to 7 days prior to secondary antigen injection will give essentially the same results.

I claim:

1. A multivalent complex suitable for blocking allergic reactions selected from the group consisting of:
   (1) a complex consisting essentially of at least one antigen D fragment bonded to a protein or peptide having the formula:

wherein
   G represents glucose;
   T represents threonine or a peptide linked to said structure through a threonine molecule; and
   R represents a peptide or protein covalently bonded to said antigen D fragment through at least one glucose moiety,
(2) a quercitin-glutathione complex having the formula:

and (3) a complex consisting essentially of at least one quercitin-glutathione complex having the formula:

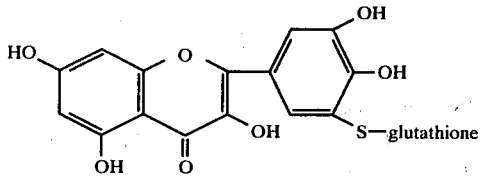

covalently bonded to a protein or peptide by a peptide linkage through the glutathione moiety.

2. A multivalent complex suitable for blocking allergic reactions comprising at least one antigen D fragment bonded to a protein or peptide and having the formula:

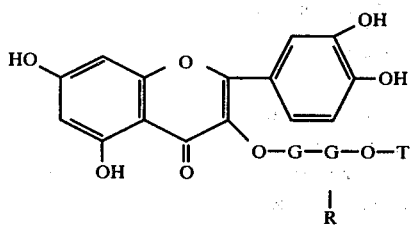

wherein:
G represents glucose;
T represents threonine or a peptide linked to said structure through a threonine molecule; and
R represents a peptide or protein covalently bonded to said antigen D fragment through at least one glucose moiety.

3. The conjugate of claim 2 wherein said peptide or protein covalently bonded to said fragment is human serum albumin, a d-amino acid copolymer of lysine and glutamic acid or human IgG.

4. The conjugate of claim 2 wherein T is a threonine containing peptide such that the molecular weight of said fragment is about 5000.

5. The conjugate of claim 2 wherein said threonine containing peptide is such that the molecular weight of said fragment is about 2500.

6. The conjugate of claim 2 wherein T represents threonine.

7. The conjugate of claim 4 wherein said fragment is covalently bonded to a d-amino acid copolymer of lysine and glutamic acid.

8. The conjugate of claim 4 wherein said fragment is covalently bonded to human IgG.

9. The conjugate of claim 4 wherein said fragment is covalently bonded to human serum albumin.

10. The conjugate of claim 5 wherein said fragment is covalently bonded to a d-amino acid copolymer of lysine and glutamic acid.

11. The conjugate of claim 5 wherein said fragment is covalently bonded to human IgG.

12. The conjugate of claim 6 wherein said fragment is covalently bonded to human serum albumin.

13. A multi-valent complex suitable for blocking allergic reactions comprising a quercitin-glutathione complex having the formula:

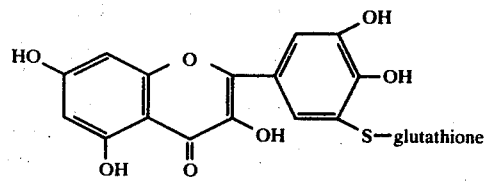

14. A multi-valent complex suitable for blocking allergic reactions comprising at least one quercitin-glutathione complex having the formula:

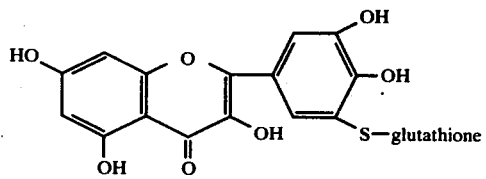

covalently bonded to a protein or peptide by a peptide linkage through the glutathione moiety.

15. The conjugate of claim 14 wherein said protein or peptide is human serum albumin, d-amino acid copolymer of lysine and glutamic acid or human IgG.

16. The conjugate of claim 14 wherein peptide is a d-amino acid copolymer of lysine and glutamic acid.

17. The conjugate of claim 14 wherein protein is human serum albumin.

18. The conjugate of claim 14 wherein protein is human IgG.

19. A method of forming the conjugate of claim 2 comprising activating the glucose moieties therein by reaction with an activating agent and reacting the thus formed intermediate with a peptide or protein.

20. The method of claim 19 wherein said activating agent is a cyanogen halide.

21. The method of claim 19 wherein said protein or peptide is human serum albumin, a d-amino acid copolymer of lysine and glutamic acid or human IgG.

22. The method of claim 21 wherein T represents threonine.

23. The method of claim 21 wherein T is a threonine containing peptide such that the molecular weight of said fragment is about 5000.

24. The method of claim 21 wherein T is a threonine containing peptide such that the molecular weight of said fragment is about 2500.

* * * * *